US009778223B2

(12) United States Patent
Schneider et al.

(10) Patent No.: US 9,778,223 B2
(45) Date of Patent: *Oct. 3, 2017

(54) SYSTEM AND METHOD FOR THE SEPARATION OF ANALYTES

(71) Applicants: Leidos, Inc., Reston, VA (US); Georgetown University, Washington, DC (US)

(72) Inventors: Thomas Wayne Schneider, Oakton, VA (US); James N. Baraniuk, Bethesda, MD (US)

(73) Assignee: Leidos, Inc., Reston, VA (US)

( * ) Notice: Subject to any disclaimer, the term of this patent is extended or adjusted under 35 U.S.C. 154(b) by 423 days.

This patent is subject to a terminal disclaimer.

(21) Appl. No.: 14/496,699

(22) Filed: Sep. 25, 2014

(65) Prior Publication Data

US 2015/0008130 A1 Jan. 8, 2015

Related U.S. Application Data

(62) Division of application No. 13/323,813, filed on Dec. 12, 2011, now Pat. No. 8,859,296, which is a division of application No. 12/644,341, filed on Dec. 22, 2009, now Pat. No. 8,097,472, which is a division of application No. 10/372,799, filed on Feb. 26, 2003, now Pat. No. 7,655,477.

(51) Int. Cl.
*G01N 33/558* (2006.01)
*G01N 27/447* (2006.01)

(52) U.S. Cl.
CPC . *G01N 27/44795* (2013.01); *G01N 27/44721* (2013.01); *G01N 27/44791* (2013.01); *G01N 33/558* (2013.01)

(58) Field of Classification Search
None
See application file for complete search history.

(56) References Cited

U.S. PATENT DOCUMENTS

| | | | |
|---|---|---|---|
| 4,834,862 A | 5/1989 | Breiner et al. | 204/301 |
| 4,927,265 A * | 5/1990 | Brownlee | G01N 21/31 204/603 |
| 5,376,252 A | 12/1994 | Ekstrom et al. | 204/603 |
| 5,538,613 A * | 7/1996 | Brumley | G01N 27/44721 204/456 |
| 5,800,692 A | 9/1998 | Naylor et al. | 204/601 |
| 6,007,690 A * | 12/1999 | Nelson | G01N 27/44791 204/450 |
| 6,074,827 A | 6/2000 | Nelson et al. | 435/6 |
| 6,103,537 A | 8/2000 | Ullman et al. | 436/526 |
| 6,200,814 B1 | 3/2001 | Malmqvist et al. | 436/52 |
| 6,274,089 B1 | 8/2001 | Chow et al. | 422/101 |
| 6,344,121 B1 * | 2/2002 | Stalcup | B01D 57/02 204/450 |
| 6,428,666 B1 | 8/2002 | Singh et al. | 204/450 |
| 6,500,323 B1 | 12/2002 | Chow et al. | 204/450 |
| 6,537,432 B1 * | 3/2003 | Schneider | G01N 27/44726 204/450 |
| 6,551,836 B1 | 4/2003 | Chow et al. | 436/149 |
| 6,589,729 B2 * | 7/2003 | Chan | B01J 19/0093 435/288.5 |
| 6,623,860 B2 * | 9/2003 | Hu | B01D 17/0208 137/833 |
| 6,676,819 B1 * | 1/2004 | Liu | C07K 1/26 204/451 |
| 6,837,977 B1 | 1/2005 | Dunayevskiy et al. | 204/451 |
| 6,905,583 B2 | 6/2005 | Wainright et al. | 204/453 |
| 7,105,356 B2 | 9/2006 | Malmqvist et al. | 436/174 |
| 7,407,568 B1 | 8/2008 | Malik et al. | 204/455 |
| 7,655,477 B1 * | 2/2010 | Schneider | G01N 33/558 436/514 |
| 8,097,472 B2 * | 1/2012 | Schneider | G01N 33/558 436/514 |
| 8,859,296 B2 * | 10/2014 | Schneider | G01N 33/558 436/514 |
| 2004/0118688 A1 | 6/2004 | Dumas | 204/548 |
| 2004/0188254 A1 * | 9/2004 | Spaid | B01F 13/0076 204/451 |
| 2004/0259269 A1 * | 12/2004 | Lin | G01N 33/561 436/516 |

OTHER PUBLICATIONS

Jan Pospichal, et al., "Analytical Aspects of Carrier Ampholyte-Free Isoelectric Focusing," *Journal of Chromatography A*, vol. 918, pp. 195-203, 2001.
C. Eggeling, et al., "Homogeneity, Transport, and Signal Properties of Single Ag Particles Studied by Single-Molecule Surface-Enhanced Resonance Raman Scattering," *The Journal of Physical Chemistry*, vol. 105, No. 15, pp. 3673-3679, Apr. 19, 2001.
Anne Chartogne, et al., "A Free-Flow Electrophoresis Chip Device for Interfacing Capillary Isoelectric Focusing On-Line With Electrospray Mass Spectrometry," *Rapid Communication in Mass Spectrometry*, vol. 14, pp. 1269-1274, 2000.
Gavin Sherlock, "Analysis of Large-Scale Gene Expression Data," *Current Opinion in Immunology*, vol. 12, pp. 201-205, 2000.
Marek Minarik, et al., "Fraction Collection in Micropreparative Capillary Zone Electrophoresis and Capillary Isoelectric Focusing," *Electrophoresis*, vol. 21, pp. 247-254, 2000.

(Continued)

*Primary Examiner* — Ann Lam
(74) *Attorney, Agent, or Firm* — Dawn-Marie Bey; Bey & Cotropia PLLC

(57) ABSTRACT

A separation module operates to fractionate or separate an analyte into fractions according to pI, i.e., pI bands, utilizing capillary isoelectric focusing ("CIEF") within a first microchannel. The fractions are stacked to form plugs, the number of which is determined by a number of parallel second microchannels integrally connected to the first microchannel, into which the fractions are directed according to the buffer characteristics found in each of the individual microchannels. Within the microchannels the plugs are separated into proteins according to a different chemical property, i.e., "m/z," utilizing capillary electrophoresis ("CE").

7 Claims, 4 Drawing Sheets

(56) References Cited

OTHER PUBLICATIONS

Ronald C. Bates, et al., "High-Performance Chromatofocusing Using Linear and Concave pH Gradients Formed with Simple Buffer Mixtures," *Journal of Chromatography A*, vol. 890, pp. 25-36, 2000.

Richard L. McCreery, "Raman Spectroscopy for Chemical Analysis," *John Wiley & Sons, Inc.*, 12pp., Copyright 2000.

Cees Bruggink, "Backgrounds and Possibilities for Electrochemical Detection in Conjunction with Anion Exchange Chromatography," *A VHAssociation—ih Symposium—Reims*, 7 pp., Mar. 2000.

A. E. Herr, et al., "Investigation of a Miniaturized Capillary Isoelectric Focusing (clEF) System Using a Full-Field Detection Approach," *Solid State Sensor and Actuator Workshop*, Hilton Head Island, SC, 5 pp., Jun. 4-8, 2000.

Hongxing Xu, et al., "Electromagnetic Contributions to Single-Molecule Sensitivity in Surface-Enhanced Raman Scattering," *Physical Review E*, vol. 62, No. 3, pp. pp. 4318-4324, Sep. 2000.

Udo Hahn, et al., "The Challenges of Automatic Summization," *IEEE*, vol. 33, No. 11, pp. 29-36, Nov. 2000.

Edward M. Marcotte, et al., "A Combined Algorithm for Genome-Wide Prediction of Protein Function," *Nature*, vol. 402, pp. 83-86, 1999.

Qinglu Mao, et al., "Capillary Isoelectric Focusing with Whole Column Imaging Detection for Analysis ofProteins and Peptides," *J Biochem. Biophys. Methods*, vol. 39, pp. 93-110, 1999.

Joel X. Rossier, et al., "Microchannel Networks for Electrophoretic Separations," *Electrophoresis*, vol. 20, pp. 727-731, 1999.

Inderjeet Mani, "Summarizing Similarities and Differences Among Related Documents," *Information Retrieval*, vol. l, pp. 35-67, 1999.

H. Georg Schulze, "Advances in Fiber-Optic Based UV Resonance Raman Spectroscopy Techniques for Anatomical and Physiological Investigations," *SPIE Conference on Biomedical Applications of Raman Spectroscopy*, San Jose, California, SPIE vol. 3608, pp. 157-166, Jan. 1999.

Jiaqi Wu, et al., "Automated Sample Introduction for an Imaged Capillary Isoelectric Focusing Instrument Via High-Performance Liquid Chromatography Sampling Devices," *Journal of Chromatography B*, vol. 714, pp. 113-188 (1998).

G. B. M. Vandeginste, et al., "Handbook ofChemometrics and Qualimetrics: Part B," *Elsevier Science B. V*, 23 pp., Copyright 1998.

D. L. Massart, et al., "Handbook of Chemometrics and Qualimetrics: Part A," *Elsevier Science B. V*, 32 pp., Copyright 1997.

Qifeng Xue, et al., "Multichannel Microchip Electrospray Mass Spectrometry," *Analytical Chemistry*, vol. 69, No. 3, pp. 426-430, Feb. 1, 1997.

Nghia Chiem, et al., "Microchip-Based Capillary Electrophoresis for Immunoassays: Analysis ofMonoclonal Antibodies and Theophylline," *Analytical Chemistry*, vol. 69, No. 3, pp. 373-378, Feb. 1, 1997.

Shuming Nie, et al., "Probing Single Molecules and Single Nanoparticles by Surface-Enhanced Raman Scattering," *Science*, vol. 275, pp. 1102-1106, Feb. 21, 1997.

Michael A. Malone, et al., "Reductive Electrochemical Detection for Capillary Electrophoresis," *Analytical Chemistry*, vol. 66, No. 21, pp. 3782-3787, Nov. 1, 1994.

Kurt Seiler, et al., "Planar Glass Chips for Capillary Electrophoresis: Repetitive Sample Injection, Quantitation, and Separation Efficiency," *Analytical Chemistry*, vol. 65, pp. 1481-1488, 1993.

Janina C. Austin, et al., "Ultraviolet Resonance Raman Studies of Proteins and Related Model Compounds," *Biomolecular Spectroscopy, Part A*, John Wiley & Sons Ltd., pp. 55-127, Copyright 1993.

Thomas M. Cover, et al., "Elements ofInformation Theory," *John Wiley & Sons, Inc.*, 22 pp., Copyright 1991.

Edmund R. Malinowski, "Factor Analysis in Chemistry," Second Edition, *John Wiley & Sons, Inc.*, 12pp., Copyright 1991.

Raymond H. Myers, "Classical and Modern Regression With Applications," *PWS-KENT Publishing Company*, 8 pp., Copyright 1990.

Andrew G. Ewing, et al., "Capillary Electrophoresis," *Analytical Chemistry*, vol. 61, No. 4, pp. 292-303, Feb. 15, 1989.

Jerome H. Friedman, "Exploratory Projection Pursuit," *Journal of the American Statistical Association*, vol. 82, No. 397, pp. 249-266, Mar. 1987.

Peter J. Huber, "Invited Paper—Projection Pursuit," *The Annals of Statistics*, vol. 13, No. 2, pp. 435-475, 1985.

Shigeki Saito, et al., "Resonance Raman Spectra (5800-40 $cm^{-1}$, of All-trans and 15-cis Isomers of 13-Carotene in the Solid State and in Solution. Measurements with Various Laser Lines from Ultraviolet to Red," *Journal of Raman Spectroscopy*, vol. 14, No. 5, pp. 299-309, 1983.

Robb J. Muirhead, "Aspects of Multivariate Statistical Theory," *John Wiley &Sons, Inc.*, 20 pp., Copyright 1982.

Rauno Virtanen, "ACTA Polytechnica Scandinavica," Chemistry Including Metallurgy Series No. 123, 34 pp., Helsinki 1974.

Richard 0. Duda, et al., "Pattern Classification and Scene Analysis," *John Wiley & Sons, Inc.*, 20 pp., Copyright 1973.

Frederick M. Fowkes, et al., "Contact Angle, Wettability, and Adhesion," Advances in Chemistry Series 43, *American Chemical Society*, 14pp., Copyright 1974.

R. J. Dijkstra, C. T. Martha, F. Ariese, U. A. Th. Brinkman, C. Gooijer, "On-Line Identification Method in Colmun Liquid Chromatography: UV Resonance Raman Spectroscopy", *Analytical Chemistry*, vol. 73, No. 20, pp. 4977-4982 (2001).

R. Tuma, G. J. Thomas, Jr., "Theory, Design, and Characterization of a Microdialysis Flow Cell for Raman Spectroscopy", *Biophysical Journal*, vol. 71, pp. 3454-3466 (1996).

M. Deshpande, K.B. Greiner, J. West, J.R. Gilbert, L. Bousse, Abdel Minalla, "Predictive Design of Reverse Injection Mechanism for Electrokinetic DNA Sample Injection", *Solid-State Sensor and Actuator Workshop*, Hilton Head Island, South Carolina, Jun. 4-8, 2000, pp. 128-131.

D. J. Harrison, K. Fluri, K. Seiler, Z. Fan, C.S. Effenhauswer, A. Manz, "Micromachining a Miniaturized Capillary Electrophoresis-Based Chemical Analysis System on a Chip", *Science*, vol. 261, pp. 895-897 (1993).

D.J. Harrison, N. Chiem, "Immunoassay Flow Systems On-Chip", *Solid-State Sensor and Actuator Workshop*, Hilton Head Island, South Carolina, Jun. 4-8, 2000, pp. 5-8.

J.Y.Qu, B.C. Wilson, D. Suria, "Concentration Measurements of Multiple Analytes in Human Sera by Near-Infrared Laser Raman Spectroscopy", *Applied Optics*, vol. 38, No. 25, pp. 5491-5498 (1999).

J. Palmer, N.J. Munro, J.P. Landers, "A Universal Concept for Stacking Neutral Analytes in Micellar Capillary Electrophoresis", *Analytical Chemistry*, vol. 71, No. 9 (1999).

K. Kneipp, H. Kneipp, R. Manaharan, E. B. Hanlon, I. Itzkan, R. R. Dasari, M.S. Feld, "Extremely Large Enhancement Factors in Surface-Enhanced Raman Scattering for Molecules on Colloidal Gold Clusters", *Societyfor Applied Spectroscopy*, vol. 52, No. 12, pp. 1493-1497(1998).

A. Woolley, D. Hadley, P. Landre, A. J. deMello, R.A. Mathies, M.A. Northrup, "Functional Integration of PCR Amplification and Capillary Electrophoresis in a Microfabricated DNA Analysis Device", *Analytical Chemistry*, vol. 68, pp. 4081-4086 (1996).

Q. Mao, J. Pawliszyn, W. Thormann, "Dynamics of Capillary Isoelectric Focusing in the Absence ofFluid Flow: High-Resolution Computer Simulation and Experimental Validation with Whole Column Optical Imaging", *Analytical Chemistry*, vol. 72, No. 21, pp. 5493-5502 (2000).

W. C. Barker, J.S. Garavelli, Z. Hou, H. Huang, R.S. Ledley, P.B. McGarvey, H.W. Mewes, B.C. Orcutt, F. Pfeiffer, A. Tsugita, C.R. Vinayaka, C. Xiao, L.L. Yeh, C. Wu, "Protein Information Resource: A Community Resource for Expert Annotation of Protein Data", *2001 Oxford University Press, Nucleic Acids Research*, vol. 29, No. 1, pp. 29-32 (2001).

W. C. Barker, J.S. Garavelli, H. Huang, P.B. McGarvey, B.C. Orcutt, G.Y. Srinivasarao, C. Xiao, L.L. Yeh, R.S. Ledley, J.F. Janda, F. Pfeiffer, H.W. Mewes, A. Tsugita, C. Wu, "The Protein Information Resource (PIR)", *2000 Oxford University Press, Nucleic Acids Research*, vol. 28, No. 1, pp. 41-44 (2000).

(56) References Cited

OTHER PUBLICATIONS

W. C. Barker, J.S. Garavelli, P.B. McGarvey, C.R. Marzec, B.C. Orcutt, G.Y. Srinivasarao, L.L. Yeh, R.S. Ledley, F. Pfeiffer, H.W. Mewes, A. Tsugita, C. Wu, "The PIR-International Protein Sequence Database", *1999 Oxford University Press, Nucleic Acids Research*, vol. 27, No. 1, pp. 39-43 (1999).

C.H. Wu, L.L. Yeh, H. Huang, L. Arminski, J.C. Alvear, Y. Chen, Z. Hu, P. Kourtesis, R. S. Ledley, B.E. Suzek, C.R. Vinayaka, J. Zhang, W. C. Barker, "The Protein Information Resource", *2003 Oxford University Press, Nucleic Acids Research*, vol. 31, No. 1, pp. 345-347 (2003).

C.H. Wu, C. Xiao, Z. Hou, H. Huang, W. C. Barker, "iProClass: An Intengrated, Comprehensive and Annotated Protein Classification Database", *2001 Oxford University Press, Nucleic Acids Research*, vol. 29, No. 1, pp. 52-54 (2001).

P.B. McGarvey, H. Huang, W. C. Barker, B.C. Orcutt, J.S Garavelli, G.Y. Srinivasarao, L.L. Yeh, C. Xiao, C.H. Wu, "PIR: A New Resource for Bioinformatics", *2000 Oxford University Press*, vol. 16, No. 3, pp. 290-291 (2000).

C.H. Wu, H. Huang, L. Arminski, J. Castro-Alvear, Y. Chen, Z. Hu, R.S. Ledley, K.C. Lewis, H.W. Mewes, B.C. Orcutt, B.E. Suzek, A. Tsugita, C.R. Vinayaka, L. L. Yeh, J. Zhang, W.C. Barker, "The Protein Information Resource: An Integrated Public Resource ofFunctional Annotation of Proteins", *2002 Oxford University Press, Nucleic Acids Research*, vol. 30, No. 1, pp. 35-37 (2002).

X. Chen, H. Wu, C. Mao, G.M. Whitesides, "A Prototype Two-Dimensional Capillary Electrophoresis System Fabricated in Poly (Dimethylsiloxane)",*Analytical Chemistry*, vol. 74, pp. 1772-1778 (2002).

Y. Shen, S.J. Berger, R.D. Smith, "Capillary Isoelectric Focusing ofYeast Cells", *Analytical Chemistry*, vol. 72, pp. 4603-4607 (2000).

P.A. Walker III, M.D. Morris, M.A. Burns, B.N. Johnson, "Isotachophoretic Separations on a Microchip-Normal Raman Spectroscopy Detection", *Analytical Chemistry*, vol. 70, pp. 3766-3769 (1998).

M. D. Koppang, M. Witek, J. Blau, G. M. Swain, "Electrochemical Oxidation of Polyamines at Diamond Thin-Film Electrodes", *Analytical Chemistry*, vol. 71, pp. 1188-1195 (1999).

D. Chen, F. Hsu, D. Zhan, C. Chen, "Palladium Film Decoupler for Amperometric Detection in Electrophoresis Chips", *Analytical Chemistry*, vol. 73, pp. 758-762 (2001).

J. Palmer, D. S. Burgi, N.J. Munro, J.P. Landers, "Electrokinetic Injection for Stacking Neutral Analytes in Capillary and Microchip Electrophoresis", *Analytical Chemistry*, vol. 73, pp. 725-731 (2001).

T.W. Schneider, H.M. Schessler, K.M. Shaffer, J.M. Dumm, L.E. Aloi, "Effects of Surface Modification on Placement and Adhesion ofNG 108-15 Cells", *Biochemical and Biomolecular Sensing, Robert A. Lieberman, Editor, Proceedings ofSPIE*, vol. 4200, pp. 22-31 (2000).

J. Klein, G. Harding, E. Klein, "A New Isoelectric Focusing Gel for Two-Dimensional Electrophoresis Constructed in Microporous Hollow Fiber Membranes", *Journal of Proteome Research*, vol. 1, pp. 41-45 (2002).

"Capillary Electrophoresis Theory and Background" [online], *CE Theory*, [retrieved on Feb. 10, 2003], 16 pp., retrieved from the Internet: http://www.ceandcec.com/cetheory.htm.

James N. Baraniuk (principal investigator), "Proteomic Prospecting by Fluidic Microsystems & Sensor Fusion," grant proposal submitted to the National Institutes of Health on Feb. 27, 2002 in response to RFP-NIH-BAA-HL-02-04.

\* cited by examiner

SYSTEM AND METHOD FOR THE SEPARATION OF ANALYTES

CROSS-REFERENCE TO RELATED APPLICATIONS

The present application is a divisional of U.S. patent application Ser. No. 13/323,813 entitled "System and Method For the Separation of Analytes," filed Dec. 12, 2011, which is a divisional of U.S. patent application Ser. No. 12/644,341 entitled "System and Method for the Separation of Analytes," filed Dec. 22, 2009, now U.S. Pat. No. 8,097,472, which is a divisional of U.S. patent application Ser. No. 10/372,799 entitled "System and Method for the Separation of Analytes," filed Feb. 26, 2003, now U.S. Pat. No. 7,655,477, which are incorporated herein by reference in their entirety.

BACKGROUND OF THE INVENTION

Field of the Invention

Generally, the invention relates to the field of analyte separation and protein detection, referred to commonly as proteomics. More particularly, the invention relates to the separation of analytes and detection of separated proteins using microfluidics and chip-based technologies.

Description of the Related Art

A key step to proteomic research is the ability to separate, isolate and independently detect proteins, i.e., hormones, enzymes, antibodies, etc. or more basically, peptides, polypeptides, amino acids and the like, within an analyte or sample (hereafter "analyte").

Heretofore, the most-widely used, but often most technically challenging, proteomic separation method is 2-dimensional isoelectric focusing ("IEF")-polyacrylamide gel electrophoresis ("PAGE") or IEF-PAGE. IEF separates proteins according to their net charge, i.e., isoelectric point ("pI") in wide pH range ampholyte buffers. The polyacrylamide gel acts as a sieve and separates analytes by Stokes' radii, i.e., molecular weight. The gel is stained to identify high and moderate abundance proteins forming spots. These spots, especially spots that change position relative to control gels, can be cut out, the proteins extracted and characterized. Extraction efficiency is on the order of 7%. Given this low extraction efficiency, IEF-PAGE is an unreliable process for protein separation.

A second approach to protein separation is high performance liquid chromatography ("HPLC"). During HPLC, mobile phase buffers under high pressure, force an approximately 1-10) μl volume of analyte through the narrow confines of specially coated, immobile silica particles. Separations are based on hydrophobicity, e.g., "reversed phase" using, for example, octadecal alkane [C-18] or other hydrophobic materials linked to silica with gradients of mobile phases such as water-acetonitrile, charge i.e., relative binding to strong cationic or anionic charged groups attached to silica, and size i.e., size exclusion chromatography. HPLC is expensive, slow and inefficient, requiring relatively large sample and solvent amounts.

Yet a third separation technique, capillary electrophoresis ("CE"), separates nanoliter ("nl") amounts of analytes according to their mass/charge ("m/z") ratios. A strong electrical potential difference pulls the analyte through an ampholyte zwitterion buffer in a long (e.g., 30 cm) capillary tube. While this technique is excellent for separation of less than 100 peptides, the ampholytes can interfere with detection processes such as ultra-violet ("UV") absorbance and mass spectrometry-mass spectrometry ("MS-MS") analysis.

Further, several miniaturized ampholyte-free modifications of CE have been developed including capillary isoelectric focusing ("CIEF") where the analytes, but not the buffer, are mobilized and separated according to pI and base stacking within the capillary tube, where NaOH or another suitable base is loaded after the sample. The electrical potential difference pulls the NaOH and any charged proteins towards the opposite end of the capillary tube. A pH gradient forms as the migrating NaOH is diluted. Individual proteins become immobilized in a narrow band at the point where they have a net neutral charge. UV-Visible ("UV-Vis") and photodiode array ("PDA") absorbance detectors can continuously monitor the separation and optimize molecular resolution, i.e., separation, to 0.002 pI units. Capillary tubes can be packed with gels or other column support materials, but these can be difficult to manufacture in a reproducible manner.

In addition to CIEF, other separation techniques which are variations on CE include separation based on size and charge differences between analytes which is termed Capillary Zone Electrophoresis ("CZE") or Free Solution CE ("FSCE"), separation of neutral compounds using surfactant which form into micelles which is called micellar electrokinetic capillary chromatography ("MECC") or sometimes referred to as ("MEKC") and sieving of solutes through a gel network commonly referred to as Capillary Gel Electrophoresis ("GCE"). Capillary electrochromatography (CEC) is an associated electrokinetic separation technique that involves applying voltages across capillaries filled with silica gel stationary phases. Separation selectivity in CEC is a combination of both electrophoretic and chromatographic processes.

Microfluidic separations are largely based on first, the electrophoretic mass transfer of the analyte and second, separation of the proteins within the analyte. The gel and ampholytes of IEF-PAGE described above for electrophoretic mass transfer are eliminated in the microfluidic microchannel and microcapillary methods. Further, reversed phase and other organic separation methods are of limited applicability when combined with a CE-based second separation step unless the solvent(s) are miscible in the CE buffer (e.g., 15% methanol buffers) and further do not separate as distinct bands, do not interfere with analyte separations or wall interactions, have low background for the detectors and are amenable to electrospray MS-MS. Separations that work at large dimensions often do not work in microsystems.

There is a need in the art for a system and method for high throughput protein separations on a micro-scale that facilitates two-dimensional separation that produces protein components that are easily detectable by recognized detector configurations.

BRIEF SUMMARY OF THE INVENTION

Summary of the Problem

Available systems and methods for analyte separation and protein detection are inefficient, expensive and unreliable due to the physical limitations of the current systems.

Summary of the Solution

A separation module operates to fractionate or separate an analyte into fractions according to pI, i.e., pI bands, utilizing capillary isoelectric focusing ("CIEF") within a first microchannel. The fractions are stacked to form plugs, the number of which is determined by a number of parallel second microchannels located orthogonally to the first microchannel, into which the fractions are directed according to the buffer characteristics found in each of the individual microchannels. Within the microchannels the plugs are separated into proteins according to a different chemical property, i.e., "m/z," utilizing capillary electrophoresis ("CE").

It is an object of the current invention to utilize microfluidics, i.e., combining silicon and polymer fabrication with the idea of liquid transfer for systems applications, in order to separate analytes into proteins and facilitate protein detection.

It is a further object of the current invention to replace current HPLC systems with a lower cost, portable, high efficiency, high throughput microfluidic system or systems that require less sample, i.e., less than 1 µl, and solvent volumes, and that provide faster and more consistent protein separations.

It is a further object of the current invention to utilize CIEF to first fractionate analytes by pI in at least one microchannel on a miniaturized chip platform that allows for analyte introduction, separation into proteins, and detection of separated proteins.

It is a further object of the current invention to utilize CE to separate the pI fractions in at least a one microchannel that is perpendicular to the at least one CIEF microchannel according to mass/charge for each protein on a miniaturized chip platform that allows for analyte introduction, separation into proteins, and detection of separated proteins.

According to a first embodiment of the present invention there is described a system for separating a sample comprising a module containing a first microchannel. Within the first microchannel, the sample is separated into a plurality of sub-samples using isoelectric focusing. A plurality of second microchannels is integrally connected to the first microchannel on the module so that the plurality of sub-samples enters at least one of the plurality of second microchannels. The constituents of these sub-samples are further separated in these second microchannels using electrophoresis.

According to a second embodiment of the present invention there is described a process for separating a sample whereby a sample is introduced into a first microchannel formed in a module. The sample constituents are separated into a plurality of sub-samples based on the varying isoelectric points of the plurality of sub-samples. The first of the plurality of sub-samples separated in the first microchannel then enters into a first of a plurality of second parallel microchannels that are integrally connected to the first microchannel. In the second microchannels, the first of the plurality of sub-samples is separated into a plurality of protein components according to electrophoresis.

According to a third embodiment of the present invention there is described a system for separating a sample. The system includes means for introducing a sample into a first microchannel formed in a module; means for separating the sample into a plurality of sub-samples based on the varying isoelectric points of the plurality of sub-samples; means for causing a first of the plurality of sub-samples to enter a first of a plurality of second parallel microchannels integrally connected to the first microchannel; means for separating the first of the plurality of sub-samples into a plurality of protein components according to electrophoresis; means for applying opposite charges to either end of the first microchannel to facilitate separating the sample into a plurality of sub-samples; means for applying a first charge to the non-intersecting end of a third microchannel integrally connected to the first microchannel and applying a second, opposite charge to the non-intersecting end of the first of the plurality of second microchannels to facilitate the first of the plurality of sub-samples entering the first of the plurality of second microchannels and further separating according to electrophoresis; means for aligning a first detector with the first microchannel in order to detect the separation of the sample into the plurality of sub-samples based on varying isoelectric points of the plurality of sub-samples within the first microchannel; means for aligning a second detector with the non-intersecting end of the first of the plurality of second microchannels; and means for detecting the plurality of protein components for the first of the plurality of sub-samples.

DESCRIPTION OF THE PREFERRED EMBODIMENTS OF THE PRESENT INVENTION

Figure 1A:
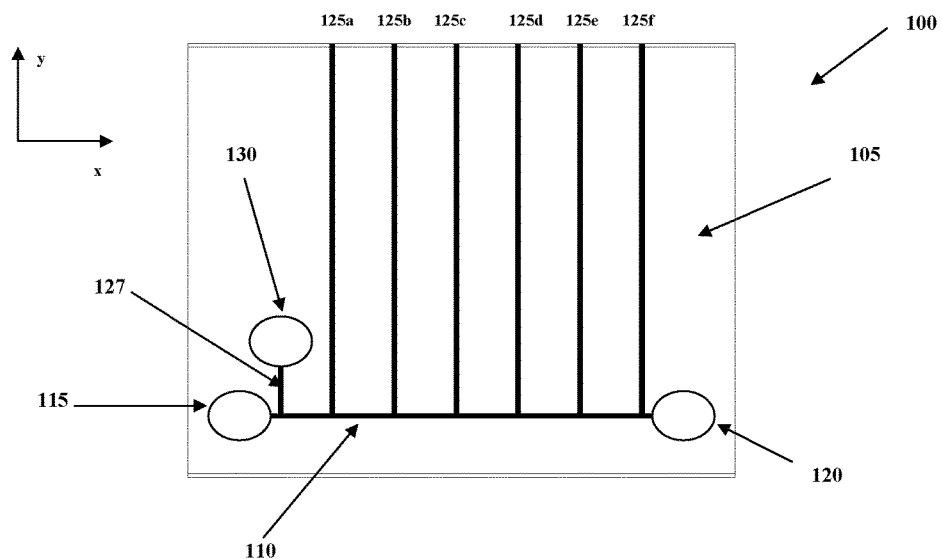
FIGS. 1(a) and 1(b) show a separation module with photodetector according to an embodiment of the present invention.
Figure 1B:
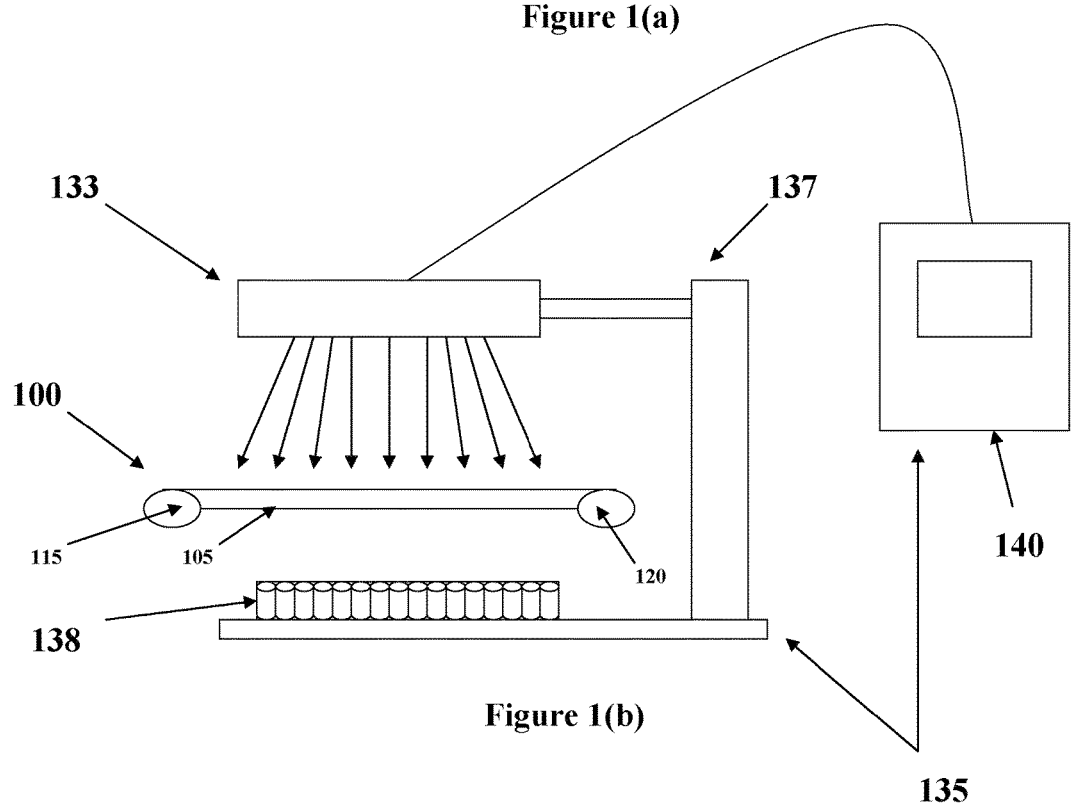
Figure 2:
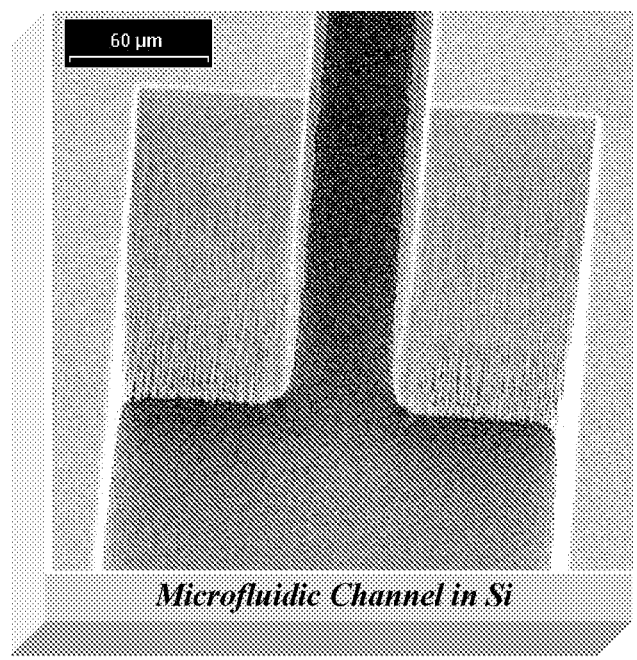
FIG. 2 shows a microchannel according to an embodiment of the present invention.

In a preferred embodiment of the present invention, CIEF and CE are combined on a semiconductor, e.g., silicon, chip forming a two-dimensional separations module 100 for facilitating two types of analyte separation and subsequent protein detection. Throughout the specification, the word protein will be used to refer to the protein molecule itself and/or one or more of its basic components, i.e., peptides, polypeptides, oligopeptides, amino acids and the like, except where specific reference is made to the individual components. As shown in FIG. 1(a), a chip 105 includes a first microchannel or microcapillary (hereafter "microchannel") 110 extending in the X direction, having reservoirs 115, 120 at opposite ends thereof. Intersecting with the first microchannel 110 are a plurality of second microchannels, 125a-f extending in the Y direction, perpendicular to the first microchannel 110. Additionally, there is a third microchannel 127 also extending in the Y direction for supplying buffer material to the system via reservoir 130. In this particular exemplary embodiment, there are six Y- direction microchannels depicted in FIG. 1(a), but the invention is not limited to six Y- direction microchannels. Microchannels 110, 125a-f and 127 are on the order of 25 to 300 µm in width. By way of example, FIG. 2 illustrates an enlarged view of a single 60 µm wide microchannel formed in silicon. Alternatively, the chip 105 may be comprised of polydimethylsiloxane ("PDMS") or other silicone-based materials and appropriate polymers. The chip 105 may be fabricated using silicon integrated circuit ("IC") processing equipment for molding the base material using negative photoresist, e.g., epoxy-based polymer SU-8. FIG. 1(b) shows a side view of the separation module 100 and a UV-Vis PDA detector 135 that includes an UV-Vis radiation source 133, a PDA 138 and an output processor/monitor 140 for tracking separations of analyte in the microchannels 110 and 125a-f. The UV-Vis source 133 and the PDA 138 are mounted on an X-Y translation stage 137 in order to be movable over and under the separation module 100 so as to scan all sections, i.e., microchannels, of the module 100.

Figure 3A:
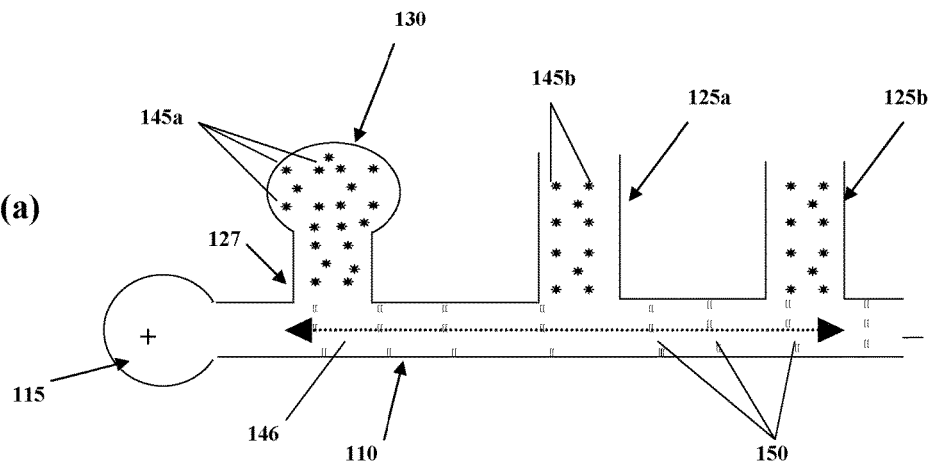
FIG. 3(a)-3(c) show two-dimensional separation steps according to an embodiment of the present invention.
Figure 3B:
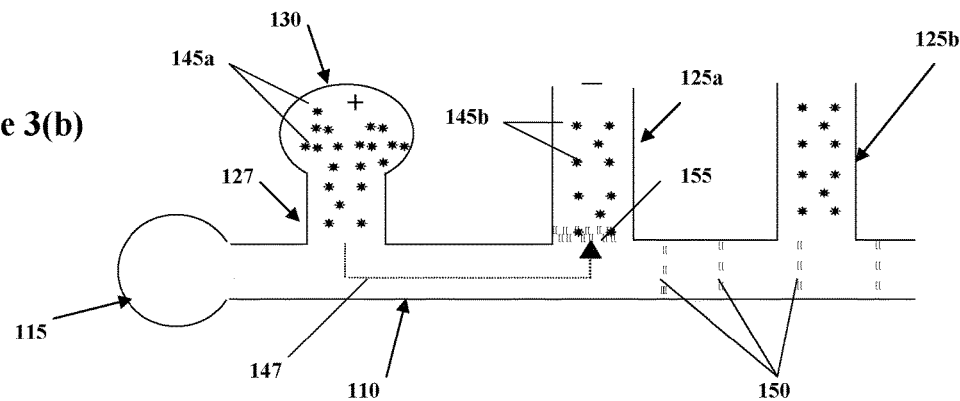
Figure 3C:
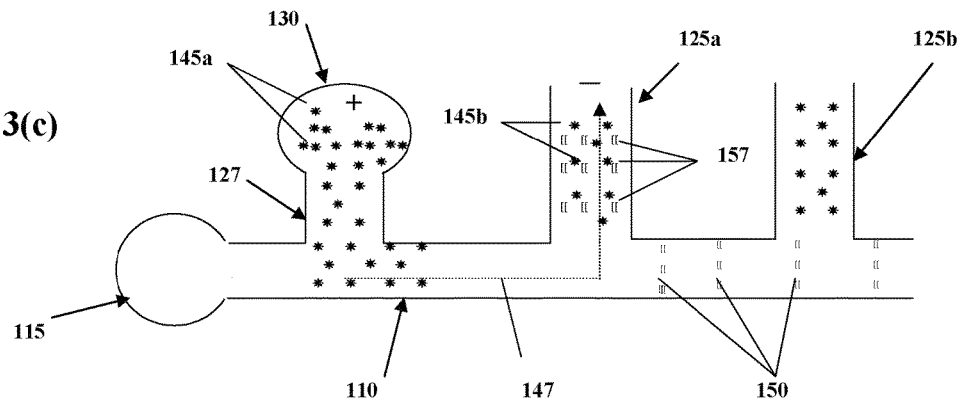

Referring to FIGS. 3(a)-(c), three exemplary, snap-shot steps of a two-dimensional separation method according to an embodiment of the present invention using the separation module 100 are shown. A predetermined amount of analyte, e.g., 1 to 500 nanoliters, is introduced into the first microchannel 110 with minimal sample carryover (i.e., less than 1%) using, for example, commercially available HPLC injection valves. Inlet and outlet ports to the separation module microchannels 110 and 125a-f may be coupled to standard high performance capillary electrophoresis coupling adapters. This configuration facilitates analyte introduction into the inlet port(s) of the separation module through microcapillary tubes. The microcapillaries are in turn attached to analyte sampling sources including, but not limited to, automated sampling devices, subcutaneous microdialysis tubes, percutaneous sampling systems, air sampling stations, microinfusion pumps, and similar or alternative devices known to those skilled in the art. The transdermal sampling device described in U.S. patent application Ser. No. 09/866,826 filed May 30, 2001, entitled "Systems and Methods for Monitoring Health and Delivering Drugs Transdermally" is an example of an appropriate analyte source. The Ser. No. 09/866,826 application is incorporated herein by reference in its entirety. Similarly, an integral outlet adapter connects the outlet port of the separation module to microcapillaries for other types of analysis including, but not limited to, mass spectroscopy, mass spectroscopy-mass spectroscopy, and other types of detection based upon any form of absorptive, fluorescent, reflective or other spectroscopy utilizing any of the range of available wavelengths, and single molecule detectors.

After the analyte is introduced into the separation module 100, reservoirs 115 and 120, containing anolyte and catholyte solutions, are driven by electrodes (not shown) supplying a voltage in the range of approximately 1-40 kV in order to facilitate the first-dimensional CIEF separation or fractionation of the analyte according to isoelectric point ("pI") along the microchannel 110 as indicated in FIG. 3(a) by line-arrow 146. The potential difference resulting from the electrodes are shown on the drawings as "+" and "−." Microchannel 127 and reservoir 130 and microchannel 125a contain buffers 145a and 145b, respectively. Additionally, the microchannels and reservoirs may contain other appropriate packing matter including gels and liquids to facilitate separation. As described above, UV-Vis PDA 135 monitors the first dimensional separation of the analyte in the first channel 110. The UV-Vis PDA 135 ascertains when sharp separations of the analyte by pI have been achieved as signified by maximum peak separation, e.g., internal standards, with no further peak movement within the system. The analyte separates according to pI into pI bands or fractions 150. The approximate time for the completion of the first dimensional separation is approximately 1 minute. This relatively short time reduces the likelihood of local Joule heating and damage to the analyte.

Turning to FIG. 3(b), once maximum peak separation is detected in microchannel 110 according to the development of a stable absorption pattern detected by UV-Vis PDA 135, voltage to the electrodes (not shown) driving reservoirs 115 and 120 are removed and voltage is supplied to the electrode (not shown) driving reservoir 130 and to ground at a second analyte detector, for example, a mass spectrometer (MS) located at the end of at least one of the perpendicular microchannels 125a-125f. By way of example, in FIG. 3(b), ground is located at the end of microchannel 125a. The application of this voltage between reservoir 130 and the end of microchannel 125a at the point of the MS detector causes the buffer 145a in the reservoir 130 to begin to move into the microchannel 110 as indicated by line-arrow 147 and directs the fractions 150 into the microchannel 125a, causing the analyte fractions 150 to base stack within the microchannel 125a between the base 145a from the reservoir 130 and the base 145b from within the microchannel 125a forming a plug 155. Buffers 145a and 145b have different compositions and ionic strengths. The base stacking relies on the difference in ionic strength between the buffers 145a and 145b. The base stacking reduces the axial distribution of plug 155 within the analyte and maintains the plug and its narrow pI set as the plug electrokinetically enters the microchannel 125a over the course of a few seconds. The stacking of each plug is critical since it ensures that each pI-separated protein is maintained as a tight peak during CE migration through microchannels 125a. This reduces the likelihood of band broadening. CE mobilities within each CIEF plug 155 vary widely so that individual proteins can be distinctly separated without overlap. Finally, as shown in FIG. 3(c), after these initial seconds, the potential difference begins to exert additional effects and separates the proteins within the plug 155 according to their mass to charge ratio ("m/z"). For example, a first plug 155 may contain proteins with pIs in the range of 9.5 to 10. These closely ordered pI bands are further separated in the CE microchannel 125a according to m/z for each protein 157.

Once the CE separation of a first plug 155 has been completed in microchannel 125a, the voltage between reservoir 130 and ground is removed and the separation module 100 and/or the microdetectors, e.g., UV-Vis PDA 135 and MS-MS, are moved using an X-Y translator in order to align the next CE microchannel 125b with the microdetectors. The voltage is applied between reservoir 130 and ground, which is now located at the end of microchannel 125b. The creation of this electrical potential difference moves buffer 145a from reservoir 130 along the CIEF microchannel 110 past CE microchannel 125a. Buffer 145a encounters a next group of analyte fractions 150 with similar pIs, e.g., 9.0 to 9.5, forms a plug 155 and pushes along the electrical gradient for separation into proteins 157 in microchannel 125b. CE separation and detection of the plug in microchannel 125b is facilitated as described above with reference to the CE separation in microchannel 125a.

This same process is repeated in series until all the plugs formed between CE microchannels 125a-f over the full length of the CIEF microchannel 110 have been eluted. While the individual plug 155 movements and CE electrophoretic separations are underway within each CE channel 125a-f, there is no net movement of the fractions 150 that have not yet been run. This is because analytes will only move down the CE microchannels 125a-f between electrodes. While Brownian motion may cause some peak broadening, this is likely to be minimal given the short time needed to run each CE microchannel and the very rapid base stacking of analytes that occurs at the mouth of each CE microchannel 125a-f when the voltage is switched to ground at the end of that particular channel.

Accordingly, in summary, the separation module 100 operates to fractionate or separate the analyte into fractions 150 according to pI, e.g., pI bands, utilizing CIEF within microchannel 110. The fractions 150 are stacked to form plugs 155, the number of which is determined by the number of parallel CE microchannels, e.g., 125a-f, into which the fractions 150 are directed according to the buffer characteristics found in each of the individual CE microchannels 125*a-f*. Within the microchannels 125*a-f* the plugs 155 are separated into proteins 157 according to a different chemical property, i.e., "m/z."

More particularly, the MS used in the exemplary embodiments described herein can be divided into three fundamental parts, namely the ionisation source, e.g., electrospray ionizer ("ESI") or matrix assisted laser desorption (MALDI); the first analyser, e.g., quadrupole, time of flight, magnet, FT-ICR; the collision chamber; the second analyzer, e.g., quadrupole, time of flight, magnet, FT-ICR; and the detector, e.g., photomultiplier, microchannel plate electromultiplier. In application to the preferred embodiment described above, the end of the microchannel currently being run is aligned with the ionization source, e.g., electrospray ionizer ("ESI") using, for example, an X-Y translator. The X-Y translator and ESI are connected using, for example, an exit-microcapillary bore coupling device. The separated proteins 157 are ionised within the ESI because ions are easier to manipulate than neutral molecules. An ion from the mass spectrum is extracted by the first analyzer of the mass spectrometer and upon exiting the first analyzer is introduced into the collision chamber that is filled with a neutral gas. Collisions occur and as a result of the shock, the ion fragments in a characteristic way, resulting in several other ions with a lower mass. The additional ions generated from the single input ion are carried to the second analyzer which separates them according to their mass (m)-to-charge (z) ratios (m/z) and a mass spectrum of the fragmented ions is obtained via the detector. The analyzer and detector of the mass spectrometer, and often the ionisation source too, are maintained under high vacuum to give the ions a reasonable chance of travelling from one end of the instrument to the other without any hindrance from air molecules.

The CE separations occurring in the CE microchannels 125*a-f* of the example described herein are based on the studies initiated by Helmholtz in the 1800's who discovered that an electric field passively transported solutes. This electroosmotic flow ("EOF") occurs when a buffer ionizes capillary inner wall silanol groups (SiO—) that attract a static layer of positively-charged cationic analytes. This forms the Inner Stern or Helmholtz layer. At a distance from this electrostatic interaction is the Outer Helmholtz Phase containing well-hydrated cations or hydration shells. Under an electric field, these hydration shells interact with the bulk water of the mobile phase and cause the entire buffer solution in the microchannels 125*a-f* cross-section to be pulled towards the negative electrode located at the end of each microchannel. This bulk flow passively carries anionic, neutral and cationic species, but separation between them occurs because the more positively charged ions migrate fastest, while negatively charged ions actually move backwards. However, the forward rate of EOF is faster than this retrograde electrokinetic movement, so all analytes are eventually separated and eluted from each of the microchannels 125*a-f*. EOF separations can be standardized using a rapidly migrating frontal marker such as Lys3TrpLys4, neutral marker (dimethyl-formamide or -sulfoxide), and slow migrating retrograde marker (e.g., normetanephrine). EOF is dependent on pH, buffer and wall coatings. For example, nn pH 9, 20 mM borate buffer, EOF is about 2 mm/sec (4 nl/s in a 50 μm inner diameter ("i.d.") capillary).

In further embodiments of the present invention, the separated proteins 157 from each of the CE microchannels 125*a-f* are assayed by a series of complementary microdetectors including, but not limited to, absorption detectors, e.g., UV-Vis PDA, low abundance polypeptide peak detection by diamond-coated carbon film redox potential, surface enhanced IR Raman spectroscopy ("SERS"), and MS-MS. A processor integrates the results from these microdetectors so that a library of MS-MS-defined proteins can be cross-referenced with unique, statistically derived combinations of factors selected from one or more of the microdetectors.

Initially, as described above, a UV-Vis PDA 135 is used to detect the CIEF separation progress within microchannel 110. This monitoring allows for receipt of instantaneous information about the progress of IEF separation, its completion, and the time to trigger the CE dimension of the 2-dimensional separation process on the separation module 100. Depending on the UV-Vis PDA configuration, the same UV-Vis PDA could be used to monitor the CE separation or, alternatively, separate UV-Vis PDAs could be used for each dimension. By monitoring the internal standards, i.e., known colored proteins, that are included in the analyte, the relative retention times and optical density of these colored proteins can be used for quality control as well as to calibrate the sensors for quantification of unknown proteins within the analyte. The UV-Vis PDA 135 outputs for analysis include relative retention time and complete UV-Vis spectra for each peak as it leaves the separation module 100 and enters the MS-MS. The UV-Vis PDA detection results are quantified and monitored for quality control using the continuous UV-Vis output of the CIEF microchannel 110 and post-CE effluent absorbance since each run should separate the internal standards in identical fashion.

In a specific example, the magnitude of the optical density at 280 nm ("OD280") is measured for the internal standards and compared to previously established quality control limits and standard curves so that all peaks with measurable OD280 can be quantified. Synthetic oligopeptides can be used to calibrate, for example, CIEF. They give sharp OD280 concentration peaks with excellent separation between pIs of approximately 3.38 to 10.17. In our exemplary embodiments, approximately μl of internal standard is added per 100 μl of analyte. Pre-stained Ultra-Low Range (1-27 kDa) and High Range (29-205 kDa) PAGE standards (e.g., from Sigma-Aldrich, St. Louis, Mo.) are mixed and diluted 1:1000 in pH 7.4 phosphate-buffered saline (PBS) before addition to the analyte. Final concentrations are about 300 pM, and although this concentration falls within the low abundance range, the internal standards are individually detectable by UV-Vis spectra because they are concentrated into narrow high intensity bands or peaks by the separation methods. Exact concentration curves of each covalently linked dye-protein complex are determined in advance from dilution curves and UV-Vis spectra. MS-MS will identify them from their nonhuman sequences. Relative retention times for every separation step will be calibrated by ascertaining UV-Vis PDA readings at critical junction points during the CIEF and CE separation times. This is important since salt concentrations and other variables can alter absolute CE and other separation retention times. Internal calibration of each separation step and detection system improves quality control, quantitative and qualitative analysis. A substantial number of internal standards that would not be detectable in the pre-separation or CIEF separated analyte become more readily detectable because of the compounding of the concentrating abilities of the 2-dimensional separation techniques.

Once CE separation has begun in at least one CE microchannel, i.e., 125*a*, the effluent from microchannel 125*a* is also detected by UV-Vis PDA 135 that scans the separation module 100 as shown in FIG. 1(*b*). As described above, the PDA 138 and associated UV-Vis source 133 are mounted on an X-Y translation stage 137. The separation module 100 may also be mounted on an X-Y micromanipulator translation stage in order to control location with respect to the UV-Vis PDA 135, MS-MS detector, and other microdetectors described below. Since the UV-Vis radiation is scanned through the separation module 100 before reaching the UV-VIS PDA 135, the separation module 100 is formed from materials that are transparent to the UV-Vis radiation, e.g., quartz chips, fused silica, plastics, and other special polymers known to those skilled in the art.

In a further embodiment of the present invention, once the effluent containing the separated proteins 157 passes through each of the CE microchannels 125*a-f*, the effluent continues past the UV-Vis PDA 135 and is drawn into the ESI of the MS-MS detector. The internal standards will also flow into the MS-MS detector. By linking the UV-Vis PDA 135 output with the relative retention time, m/z, and MS-MS signal amplitude, signal intensity amplitude can be calibrated for individual peaks. These serve as secondary measures of concentration for unknown proteins. This interpolation is especially valuable for low abundance proteins. Completion of analyte elution is defined by a return to baseline output of both the UV-Vis PDA 135 and the MS-MS detector. Time series data for the first microchannel, e.g., 125*a*, CE run is collated according to the internal standards.

As referenced above, in an embodiment of the present invention, MS-MS is utilized to identify proteins through the generation of mass spectrograms. Each mass spectrogram contains time series data for the proteins flowing sequentially from the CE microchannels 125*a-f* and multiple detector modules through the ESI. Each MS-MS peak is identified by its retention time, signal intensity, and mass/charge (m/z) ratio. The versatility of the MS-MS system is that once one ion has been characterized, the processor, running MS-MS-specific commercially available software, automatically searches for other ions in the ionized stream. As many as 5 "cuts" can be made at millisecond intervals, resulting in the identification of numerous separate MS-MS peaks that would represent low abundance proteins hidden within a single higher abundance peak. Identification of these low abundance proteins would have been lost in the higher abundance peak as detected by other microdetectors. The three data points including: normalized retention time (Rt); signal intensity, which is a surrogate of concentration; and m/z, which is a composite indicator of charge and mass, define the coordinates for a single MS peak. Appropriate commercial, equipment-specific information processing software generates a printout of retention time, intensity, and m/z for all the peaks from a given separation run. This data forms a matrix or vector that characterizes this unique separation run and analyte. These matrices or vectors, as opposed to the protein sequences of every MS-MS peak, represent the data format that is exported for detector or sensor fusion, described below, and can ultimately be used for the statistical search for endpoints including, but not limited to: all the proteins in the original sample; a select set of proteins having specific MS peak coordinates; MS-MS derived identification of the amino acid sequences of all the proteins in a sample; the specific MS and/or MS-MS peaks that are common between 2 or more sets of samples, different between 2 or more sets of samples, that have a common source (e.g., all human proteins, all bacterial proteins, or other subsets of the MS-MS database from any given run), or specific MS and/or MS-MS peaks that are common to a specific disease or condition. This pattern may include peaks that are absent, decreased, increased, or induced compared to a control (e.g., normal) sample. This pattern is often referred to as the disease-specific biosignature.

By way of specific example, in a particular exemplary embodiment of the present invention, after the first analyzer step of the MS-MS detection, in the second analyzer step of the MS-MS detection, the resulting charged proteins are turned orthogonally, fragmented into all potential contiguous peptides and amino acids, and the m/z of each is determined by time of flight ("ToF"). This MS-MS detection configuration is useful for sequencing short peptides. In order to obtain more specific sequence data for intact proteins, in a preferred embodiment, trypsin digests of fractionated specimens are used to obtain protein identities. Trypsin digests are run by standardized size exclusion, i.e., reversed phase 2-dimensional HPLC. Both intact and trypsin digested MS-MS data are entered into the electronic library for comparison to future samples, their peaks, and potential biomarker peaks and biosignatures patterns. Further still, sequenced peptides may be identified through comparison of the collected data from the 2-dimensional separation technique described herein to data that has been collected and catalogued previously. For example, Georgetown's Protein Information Resource ("PIR") serves as an integrated public bioinformatics resource. PIR provides many protein databases and data analysis tools, and employs a family classification approach to facilitate protein annotation and data integration. The PIR-NREF ("non-redundant reference") protein database provides comprehensive data collected from all major protein databases with composite protein names and bibliography information for about 800,000 proteins. Similarly, the iProClass ("integrated Protein Classification"), developed to address the database interoperability issue arising from the voluminous, heterogeneous, and distributed data, integrates information from various source databases. iProClass provides a comprehensive description of proteins including classification at the superfamily, family, domain, and motif levels, structural and functional classifications and features, as well as links to over 40 databases of protein families, structures, functions, genes, genomes, literature, and taxonomy. Such integrated data analysis is important in revealing functional associations such as protein-protein interactions.

In a further embodiment of the present invention, other micro detectors may be added in series with the UV-Vis PDA 135 at the end of the CE microchannels 125*a-f*, immediately at the ESI MS-MS connection. For example, a diamond redox potential detector is used to electrochemically detect proteins. Typical electrochemical detectors are planar solid electrodes of inert metals with unsaturated d-orbitals, like Pt, Au, and Ag. When an electrical potential is applied, the electrode will accept or donate electrons to compounds that come in contact with the surface. If used in this case, this might lead to analyte adsorption or precipitation, fouling of the electrode surface, i.e., corrosion, and ultimately a loss in signal, especially at high oxidation potentials. However, diamond coatings use OH to catalyze the oxidation of polyamines at moderate reduction-oxidation ("redox") potentials. Consequently, the amines of amino acids, peptides and proteins are excellent candidates for diamond electrode electrochemical detection in CE. CE has higher efficiency and lower volume requirements than, for example, HPLC methods, so more sensitive detection methods are required. Very low analyte concentrations, e.g., attomoles to zeptomoles, can be detected by fluorescence, but this requires analyte derivatization. Instead, CE and electrochemical detection, i.e., using a diamond redox potential detector, are ideally suited for each other because they offer even greater sensitivity without sample preparation, greater ease of miniaturization, and analyte detection at the sensor surface so that it is independent of microchannel geometry. Electrochemical detection is better suited to CE than HPLC since deoxygenation of the system is significantly shorter for CEEC versus HPLC. In a particular embodiment, diamond-coated carbon film electrodes are integrated into the separation module 100 for electrochemical detection. Shielding methods are employed to decouple the high electric field interference that is generated during CE. The diamond redox potential detector can be used to detect and quantify catecholamines, glutamate, and other amino acids, sugars, peptides, polypeptides, amine-containing lipids and other protein analytes as they pass the diamond redox potential detector. The data output for further analysis will be the electrochemical potentials and relative retention times for all detectable signals.

In a further embodiment of the present invention, Raman spectroscopy is used to detect and identify analytes. Monochromatic light striking a material will scatter elastically, e.g., with little to no energy loss, and inelastically. Part of the inelastic scattering arises from the Raman effect, in which a virtual excited state is created, which then emits a second, lower energy photon. The difference in energy corresponds to a vibrational excitation of the molecule, resulting in an emission spectrum of peaks similar to that from infrared ("IR") spectroscopy. Raman spectroscopy is ideal for use with aqueous systems, since O—H bonds of water interfere with IR spectroscopy. Using a technique called resonance Raman, Raman scattering is enhanced by up to five orders of magnitude because excitation energies are near the bond electronic transition energies. UV excitation and detection is used for resonance effects in proteins to decrease the generation of signal degrading fluorescence effects. Using surfaced enhanced Raman spectroscopy ("SERS"), Raman scattering and signal enhancement occurs when the analytes are near certain metal surfaces. Since the detection limits are near the single molecule scale, resonance Raman and SERS may be used to detect and identify protein conformations, interactions, and specific enzymatic reaction kinetics. Near infrared Raman spectroscopy may be used to quantify triglycerides, glucose and albumin in human serum. Further, fiber optic Raman spectroscopy can be used for protein identification, while normal and UV resonance Raman ("UVRR") can been used to identify effluents from conventional liquid column chromatography.

Raman spectroscopic measurements are the relative retention times and Raman spectra for all peaks within each analyte. This output is trained in protein recognition using the detailed information from the MS-MS, and aids the mass spectrometer in classifying unknowns. In an alternative embodiment, the use of Raman spectroscopy and resulting Raman spectroscopic measurements replaces the MS completely with a trained fused sensor system. Without running through the 2-dimensional, CIEF and CE, separations on the separation module 100, the concentrations of low-abundance species in an analyte are beyond the detection limits of conventional Raman spectrometers. After running through the separation module 100 the analyte generates greatly enriched, very narrow bands of proteins for detection by the Raman detector. The Raman spectra can be taken at a fixed point and time downstream from more sensitive sensors (e.g., electrochemical) and upstream from the MS-MS to ensure that a band is present during spectral measurement.

In a particular embodiment of the present invention, SERS is utilized with the separation module 100 in order to obtain single molecule Raman spectra. SERS relies on interactions between proteins and a metal surface. Since the molecules need to be stopped relative to the metal, a microchannel bifurcation is inserted into the separation module. The flowing effluent stream mixes with, for example, Au or Ag colloid nanoparticles, before passing through the Raman sampling volume for detecting the analyte interactions with the Au or Ag.

In a further embodiment of the present invention, there is provided a data reduction and analysis strategy for reducing and analyzing the analyte data generated by the multiple detectors described above during the detection process following the 2-dimensional separation process. The multiple analytical detectors, e.g., MS-MS, UV-Vis PDA, SERS, and diamond redox potential, generate many dimensions of analyte data. For a given analyte, it is possible to measure thousands of variables. Because the population size is smaller than the number of variables, spurious correlations occur if the data is not properly reduced.

Figure 4:
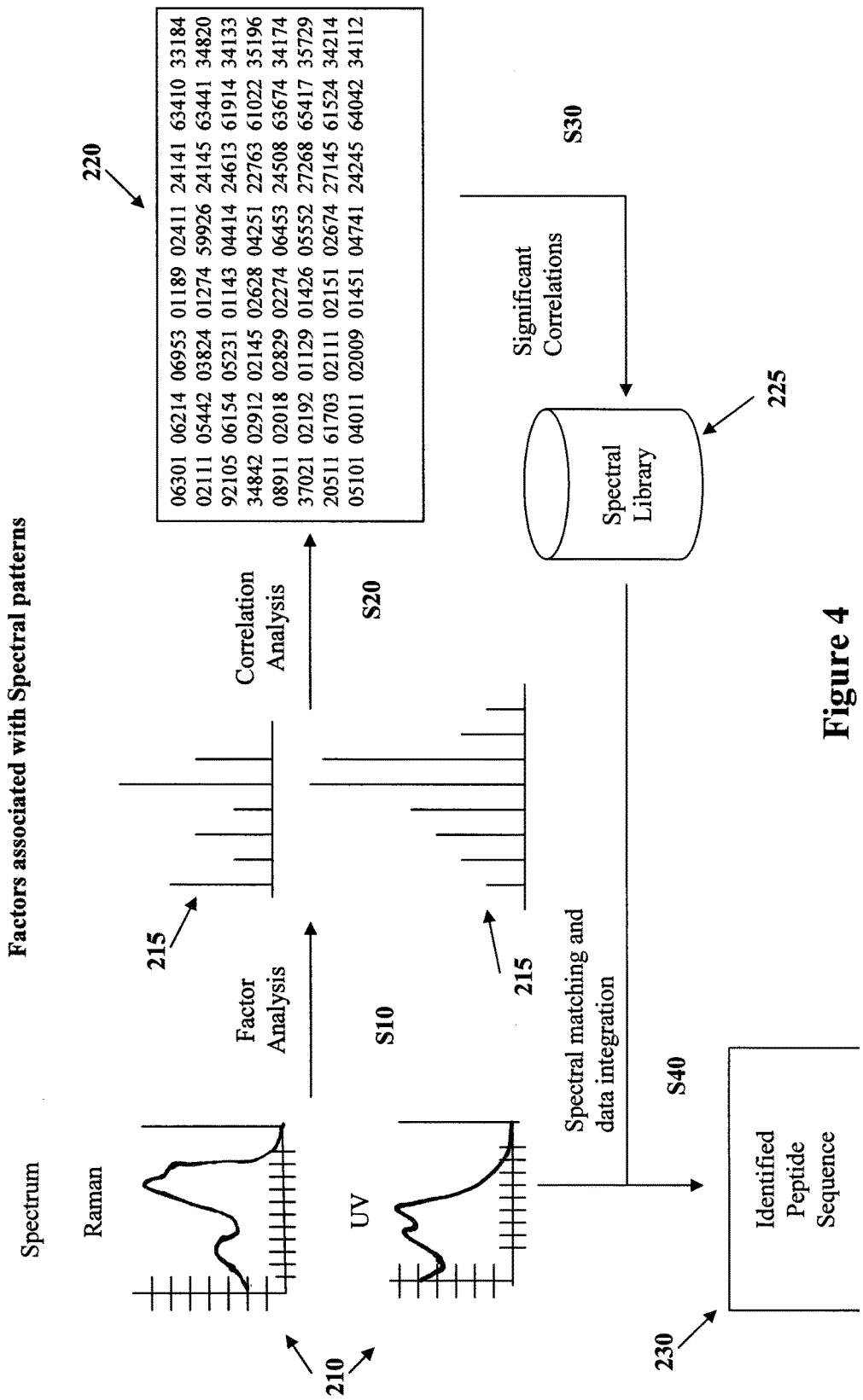
FIG. 4 shows a method for reducing data according to an embodiment of the present invention.

Referring to FIG. 4, the reduction method according to this embodiment combines knowledge-based variable selection, factor analysis, and decision-level data fusion. A spectrum from a given detector, e.g., Raman, UV, 210 is initially reduced in size by discarding peaks or bands that are known to be physically uninformative, such as water absorption bands in the UV-Vis spectrum or known contaminant peaks in the MS-MS spectra. Next, multivariate factor analysis techniques S10 are employed to reduce the dimensionality. As an example, a Karhunen-Loeve ("KL") transform may be applied, also known as Principal Components Analysis, or PCA to a collection of spectra from an MS-MS experiment. The KL transform is an orthogonal transformation matrix that consists of the eigenvectors of the variance-covariance matrix, and is used to remove linear correlations. The result of the factor analysis S10 is a set of transformed spectra 215 where each transform variable/factor is a linear combination of all the original variables, and is associated with a distinct spectral pattern. In this embodiment, only variables associated with non-zero eigenvalues are retained, resulting in a further dimensionality reduction.

Other factor analysis techniques that can be applied to this problem include multiple regression, partial least squares, discriminant analysis and projection pursuit. As a result of the factor analysis step S10, the number of variables/factors is no more than the number of proteins. Next, the individual variables are subject to correlation analysis S20 for possible correlations 220. As a subset of the correlation analysis, a second variable reduction step is performed by applying a univariate quality measure, such as information-theoretic entropy, to each remaining variable and discarding those with low quality. Using MS-MS data as the reference standard, a search is conducted for correlations that can ultimately be exploited to identify proteins in the analyte. The reduced variable set from the correlation analysis S20 for each analytical method is compared to the MS-MS variable set in a cross-correlation matrix. Each position in the matrix represents the pair-wise linear correlation coefficient. The correlation coefficients follow a Wishart distribution. A likelihood ratio test is applied to determine the significance level of each correlation coefficient S30. A protein signature library 225 is developed using the analytical methods as applied to the various detector outputs and correlations that show significance above a pre-set threshold are retained for careful "by hand" analysis S40, using visualization and clustering techniques, resulting in the linking of the spectral signatures to specific sequences 230.

Clustering tools that are typically used in proteomics and gene expression analysis include hierarchical clustering, K-means clustering and self-organizing maps. In addition to pair-wise linear correlations, other high-order or other non-linear correlations can be used to link spectra. As a protein signature library is developed using UV-Visible PDA, SERS, and other analytical methods, the comparison between unknown samples and library spectral signatures is possible. This comparison can be performed using established multivariate distance measures, e.g., Euclidean distance, Pearson correlation, Eisen's un-centered correlation. The use of multiple signature databases increases the confidence level on matches by providing independent sources of evidence.

In a further embodiment of the present invention, advanced multi-detector molecular identification is facilitated by combining analytical data from multiple detectors at the decision level. Decision level fusion takes as its input binary, i.e., yes/no decisions with associated confidence levels, or soft decisions in the form of probabilities or beliefs. Decisions about the identity of a peptide from multiple instruments is combined by using an appropriate combination rule such as Bayes', Dempster's or fuzzy logic. Performing the data integration at the decision level allows for the overall search strategy to be modular, so that any subset of analytical methods can be applied for a particular experiment without the need to re-design the algorithm.

The systems and methods described herein will find use in at least the technology areas of: proteomics; lab-on-chip; biological agent detection; on-line assessments of analytes in critically ill patients (e.g., monitors in intensive care units) to give real-time concentrations of sensitive markers of myocardial infarction, bacterial, viral, fungal or other human or animal local or systemic infections, immunologic or other injury; real-time processing or manufacturing quality control assessments; portable and robust detectors for distant monitoring of air, water, or other environmental factors with radio-linked communication to central monitoring facilities; nuclear reactor or other sites inaccessible to human inspection for detection of normal, abnormal or contaminated products for safety and quality control; fermentation process assessment and quality control; and any other conceivable application where the exact constituents of a sample must be monitored.

The embodiments described herein are intended to be exemplary and are in no way intended to limit the scope of the invention. One skilled in the art recognizes the variations to the embodiments described herein that fall within the scope of this description.

The invention claimed is:

1. A system for separating a sample comprising:
   injection adapters that introduce a sample into a first microchannel formed in a module;
   a first microchannel of the module that separates the sample into a plurality of sub-samples based on varying isoelectric points of the plurality of sub-samples, the first microchannel having an isoelectric focusing buffer with a first ionic strength formed therein;
   at least one second microchannel that separates a first of the plurality of sub-samples into a plurality of protein components according to electrophoresis, the at least one second microchannel having an electrophoresis buffer with a second ionic strength therein, wherein the second ionic strength of the electrophoresis buffer is different from the first ionic strength of the isoelectric focusing buffer;
   electrodes that apply opposite charges to either end of the first microchannel to facilitate separating the sample into the plurality of sub-samples;
   a translator that aligns a first detector with the first microchannel to detect the separation of the sample into the plurality of sub-samples based on varying isoelectric points of the plurality of sub-samples within the first microchannel, and aligns a second detector with one microchannel of the at least one second microchannel.

2. The system according to claim 1, wherein the first detector comprises UV-Visible ("UV-Vis") and photodiode ("PDA") arrays.

3. The system according to claim 2, wherein the UV-Vis and PDA arrays continuously monitor the separation of the sample into the plurality of sub-samples.

4. The system according to claim 1, wherein each of the plurality of sub-samples contains at least one known component and at least one unknown component.

5. The system according to claim 4, wherein the at least one known component is an internal standard and the at least one unknown component is a protein component.

6. The system according to claim 5, wherein the protein component is at least one of an amino acid, a peptide, a polypeptide or a protein.

7. The system according to claim 1, wherein the second detector is a mass spectrometer that produces a spectrum indicative of each of the plurality of protein components.

* * * * *